United States Patent
Boyce (10) Patent No.: US 6,538,008 B1
(45) Date of Patent: Mar. 25, 2003

(54) COMBINATION OF A SELECTIVE NMDA NR2B ANTAGONIST AND AN OPIOID ANALGESIC

(75) Inventor: Susan Boyce, Bishops Stortford (GB)

(73) Assignee: Merck Sharpe & Dohme Limited (GB)

( * ) Notice: Subject to any disclaimer, the term of this patent is extended or adjusted under 35 U.S.C. 154(b) by 0 days.

(21) Appl. No.: 09/622,733

(22) PCT Filed: Feb. 26, 1999

(86) PCT No.: PCT/GB99/00585

§ 371 (c)(1),
(2), (4) Date: Aug. 22, 2000

(87) PCT Pub. No.: WO99/44610

PCT Pub. Date: Sep. 10, 1999

(30) Foreign Application Priority Data

Mar. 6, 1998 (GB) ............................................. 9804885

(51) Int. Cl.$^7$ ........................ A61K 31/445; A61K 31/44
(52) U.S. Cl. ........................ 514/317; 514/315; 514/282; 514/280
(58) Field of Search ................. 514/317, 315, 514/282, 280

(56) References Cited

U.S. PATENT DOCUMENTS

| 3,509,164 A | 4/1970 | Carron |
| 4,690,931 A | 9/1987 | Wick et al. |
| 5,668,121 A | 9/1997 | Bigge et al. |
| 6,194,000 B1 * | 2/2001 | Smith et al. .................. 424/458 |
| 6,218,404 B1 * | 4/2001 | Bigge et al. ................. 514/317 |

FOREIGN PATENT DOCUMENTS

| EP | 0 109 317 | 5/1984 |
| EP | 0 648 744 | 4/1995 |
| EP | 0 768 086 | 4/1997 |
| FR | 89 04835 | 9/1989 |
| WO | WO 97/13769 | 4/1997 |

OTHER PUBLICATIONS

"Blockade of the plyamine site of NMDA receptors produces antinociceptio and enhances the effect of morphine, in mice", Bernardi et al., Eur. J. Pharmacol. 1996, 298(1), 51–5.*
"Prolongation of morphine analgesia by competitive NMDA receptor antagonist d–CPPene (SDZ EAA 494) in rats", Bespalov et al., European Journal of Pharmacology, 351, 12998, 299–305.*
"combined opioid–NMDA antagonist therapies. What advantages do they offer for the control of pain syndromes?", Wiesenfeld–Hallin Z, Drugs, 1998, 55(1) 1–4, abstract.*
A.H. Dickenson, Trends Pharmacol. Sci., 11:307–309 (1990).
Ishii, et al., J. Biol. Chem., 268:2836–2843 (1993).
Kristensen, et al., Pain 51:249–253 (1992).
Price, et al., Pain 59:165–174 (1994).
Max, et al., Clin. Neuropharmacol., 18:360–368 (1995).
Price, et al., Pain 68:119–127 (1996).
Mao, et al., Pain 67:361–368 (1996).
Taniguchi, et al., B.J. Pharmacol., 122:809–812 (1997).
R. Hill, Esp. Opin. Invest. Drugs, 5:1549–1562 (1996).
B.H. Manning, et al., Pain, 67:79–88 (1996).
P. Avenet, et al., Neuroscience Lett. 223:133–136 (1997).

* cited by examiner

Primary Examiner—Zohreh Fay
Assistant Examiner—Brian-Yong S. Kwon
(74) Attorney, Agent, or Firm—David Rubin; David L. Rose (57) ABSTRACT

A combination of a selective NMDA NR2B antagonist and an opioid analgesic is useful in the treatment of pain or nociception.

6 Claims, 3 Drawing Sheets

Figure 1
Inhibition of carrageenan-induced mechanical hyperalgesia by the NMDA NR2B antagonist RO25-6981 in rats

*p<0.05 compared to Carrageenan/vehicle

Figure 2
Effect of combination of morphine with the NMDA NR2B antagonist Ro25-6981 on carrageenan-induced hyperalgesia

(Ro25-6981 1 mg/kg i.p.)

\* p < 0.05 compared to vehicle treated

+ p < 0.05 compared to morphine alone

Figure 3
Effect of morphine alone and in combination with the NMDA NR2B antagonist Ro25-6981 on motor co-ordination on the accelerating rotorod

COMBINATION OF A SELECTIVE NMDA NR2B ANTAGONIST AND AN OPIOID ANALGESIC

This is an application under 35 U.S.C. 371 of PCT/GB99/00585 and claims priority from Great Britain Application No. 9804885.3, filed Mar. 6, 1998.

This invention relates to the treatment or prevention of pain or nociception by the administration of a combination of a selective NMDA NR2B antagonist and an opioid analgesic.

Pain has been defined as the sensory experience perceived by nerve tissue distinct from sensations of touch, pressure, heat and cold. It is often described by sufferers by such terms as bright, dull, aching, pricking, cutting, burning, etc. This range of sensations, as well as the variation in perception of pain by different individuals, renders a precise definition of pain near impossible. Pain as suffering, however, is generally considered to include both the original sensation and the reaction to that sensation. Where pain is "caused" by the stimulation of nociceptive receptors and transmitted over intact neural pathways, this is termed nociceptive pain. Alternatively, pain may be caused by damage to neural structures, often manifesting itself as neural supersensitivity, and is classed as neuropathic pain.

The level of stimulation at which pain is perceived is referred to as the "pain threshold". Where the pain threshold is raised, for instance, by the administration of an analgesic drug, a greater intensity or more prolonged stimulus is required before pain is experienced. Analgesics are a class of pharmaceutical agent which, following administration to a patient in need of such treatment, relieve pain without loss of consciousness. This is in contrast to other pain-relieving drugs, for example, general anaesthetics which obtund pain by producing a hiatus in consciousness, or local anaesthetics which block transmission in peripheral nerve fibres thereby preventing pain.

NMDA (N-methyl-D-aspartate)-type glutamate receptors are believed to play a pivotal role in the transmission of excitatory signals from primary sensory neurones to the brain through the spinal cord (A. H. Dickenson (1990) Trends Pharmacol. Sci., 11. 307–309). NMDA receptors mediate $Ca^{2+}$ influx into neurones, and its receptor-gated channel activity is blocked by $Mg^{2+}$ in a voltage-dependant manner. Subunits of the NMDA receptors are classified into two gene families, i.e., NR1 and NR2. A variety of compounds have been designed as antagonists targeting these subunits of the NMDA receptor for the treatment of neurodegenerative disorders, as well as acute and/or chronic pain and hyperalgesia. The NR2B subunit is predominantly expressed in the hippocampus (Ishii et al., (1993), J. Biol. Chem. 268, 2836–2843).

NMDA antagonists such as ketamine, dextromethorphan and CPP are known to have analgesic properties in man. However, these agents also induce unacceptable side-effects including hallucinations. dysphoria and cognitive and motor disturbances (see Kristensen et al., 1992, Pain, 51, 249ff, Price et al., 1994, Pain, 59, 165ff and Max et al., Clin. Neuropharmacol., 118, 360ff). In preclinical studies, dextromethorphan has been reported to potentiate the antinociceptive effects of NSAIDS and morphine (Price et al.,1996, Pain, 68, 119–127; Mao et al., 1996, Pain, 67, 361–368). However, since dextromethorphan can induce adverse effects at analgesic doses in man, it is not clear from these studies whether such combinations would still be dogged with unwanted side-effects.

One selective NMDA NR2B antagonist CP-101,606 is known to possess anti-nociceptive activity, see Taniguchi et al., B. J. Pharmacol., 1997, 122, 809–812. Potent analgesic activity of this compound was shown in rat hyperalgesic and nociceptive tests at doses showing no behavioural abnormality.

There is, however, no general teaching in the art that all selective NMDA NR2B antagonists are useful as analgesics, nor that they have improved motor side-effect profile compared to NMDA/glycine antagonists. Evidence for this is, for the first time, provided herein.

Furthermore there is no suggestion in the art that selective NMDA NR2B antagonists could potentiate the effects of opioids, such as morphine, thus providing analgesia with suprisingly reduced side-effects, such as motor-impairment. Thus the safety margin for the use of opioids, such as morphine, is surprisingly improved. There is no indication in the art relating to NMDA antagonists that the property of potentiating the action of morphine could be transferred to compounds selective for the NR2B subunit.

As the present specification surprisingly demonstrates that selective NMDA NR2B antagonists possess antinociceptive effects in rat models of inflammatory and neuropathic pain with a much improved side-effect window over non-competitive NMDA antagonists (ataxic/antinociceptive), when combined with an opioid, the combination is better tolerated than expected.

The opioid analgesics are a well-established class of analgesic agent. They are also sometimes referred to as opiates although this term should be reserved for chemical relatives of morphine. The term opioid is generally accepted to refer in a generic sense to all drugs, natural or synthetic, with morphine-like actions. The synthetic and semi-synthetic opioid analgesics are derivatives of five chemical classes of compound: phenanthrenes; phenylheptylamines; phenylpiperldines; morphinans; and benzomorphans. Pharmacologically these compounds have diverse activities, thus some are strong agonists at the opioid receptors (e.g. morphine); others are moderate to mild agonists (e.g. codeine); still others exhibit mixed agonist-antagonist activity (e.g. nalbuphine); and yet others are partial agonists (e.g. nalorphine). Whilst an opioid partial agonist such as nalorphine, (the N-alkyl analogue of morphine) will antagonise the analgesic effects of morphine, when given alone it can be a potent analgesic in its own right.

Of all of the opioid analgesics, morphine remains the most widely used and is a suitable archetype compound. Unfortunately, apart from its useful therapeutic properties, morphine also has a number of drawbacks including sedation, respiratory depression, decreased gastrointestinal motility (resulting in constipation) and, in some individuals, nausea and vomiting may occur. Another characteristic is the development of tolerance and physical dependence which mast limit the clinical use of such compounds. There is therefore a need to develop methods which enable the clinician to use lower doses of opioid analgesics such as morphine, thereby reducing the likelihood of adverse effects and development of tolerance and dependence, and thus avoiding the major problem of drug withdrawal associated with cessation of administration.

DESCRIPTION OF THE INVENTION

The present invention accordingly provides the use of a selective NMDA NR2B antagonist and an opioid analgesic for the manufacture of a medicament for the treatment or prevention of pain or nociception.

The present invention also provides a method for the treatment or prevention of pain or nociception, which method comprises administration to a patient in need of such treatment an amount of a selective NMDA NR2B antagonist and an amount of an opioid analgesic such that together they give effective pain relief In a further aspect of the present invention, there is provided a pharmaceutical composition comprising a selective NMDA NR2B antagonist and an opioid analgesic, together with at least one pharmaceutically acceptable carrier or excipient.

It will be appreciated that the selective NMDA NR2B antagonist and opioid analgesic may be present as a combined preparation for simultaneous, separate or sequential use for the treatment or prevention of pain. Such combined preparations may be, for example, in the form of a twin pack.

In a further or alternative aspect of the present invention, there is therefore provided a product comprising a selective NMDA NR2B antagonist and an opioid analgesic as a combined preparation for simultaneous, separate or sequential use in the treatment or prevention of pain or nociception.

The compositions of the present invention are useful for the treatment of pain of any eitiology, including acute and chronic pain and any pain with an inflammatory component. Examples of acute pain include, in particular, post-operative pain, migraine, headache and trigeminal neuralgia. Examples of chronic pain include. in particular, pain associated with musculo-skeletal disorders such as rheumatoid arthritis, osteoarthritis, ankylosing spondylitis, sero-negative (non-rheumatoid) arthropathies, non-articular rheumatism and peri-articular disorders, and pain associated with cancer, peripheral neuropathy and post-herpetic neuralgia. Examples of pain with an inflammatory component (in addition to some of those described above) include rheumatic pain, dental pain and dysmenorrhoea.

The compositions of the present invention are especially useful for the treatment of pain where the use of an opioid analgesic is generally prescribed. By the use of a combination of a selective NMDA NR2B antagonist and an opioid analgesic in accordance with the present invention, it is now possible to treat pain with a sub-maximal dose of an opioid analgesic thereby reducing the likelihood of side-effects associated with opioid analgesic usage (e.g. respiratory depression, constipation, nausea and vomiting, and tolerance and dependence and the associated problem of drug withdrawal).

A particularly preferred use for a composition of the present invention is in the treatment or prevention of post-operative pain.

Selective NMDA NR2B antagonists of use in the present invention include eliprodil (and those of EP-A-109317 and French utility certificate FR 89 04835), ifenprodil (and those of French patent FR 5733 M), Ro25-6981 (and those of EP-A-648744), compounds disclosed in WO-A-9713769 to Pharmacia and CP-101,606 (and those of EP-A-768086). A particularly favoured compound is Ro25-6981:

Particularly suitable selective NMDA NR2B antagonists can be identified by the following cascade which forms a further feature of the present invention. There is accordingly provided an assay for identifying a selective NMDA NR2B antagonist comprising:

(i) determining a compound having an $IC_{50}$ of less than 100 nM affinity at the human NMDA NR2B receptor and having a greater than 100-fold selectivity for NR2B receptors over human $I_{(Kr)}$ cardiac potassium channels in radioligand binding studies;

(ii) demonstrating said compound inhibits hyperalgesia with $ID_{50}$<30 mg/kg i.p. or s.c. and has a greater than 10-fold window between doses producing antinociception and motor disruption in carrageenan-induced hyperalgesia in rats;

(iii) determining said compound has an $ID_{50}$ of less than 30 mg/kg i.p. or s.c. in the rat sciatic nerve ligation assay of neuropathic pain;

(iv) determining said compound has an $ID_{50}$ of less than 30 mg/kg p.o. in the rat carrageenan-induced hyperalgesia assays; and (vi) demonstrating said compound has synergistic antinociceptive effects in combination with an opioid in an assay of nociception such as inhibition of hyperalgesia induced by carrageenan or Freund's adjuvant or inhibition of allodynia in neuropathic rats.

The compounds of use in this invention may have one or more asymmetric centres and can therefore exist as enantiomers and possibly as diastereoisomers. It is to be understood that the present invention relates to the use of all such isomers and mixtures thereof.

Suitable pharmaceutically acceptable salts of the selective NMDA NR2B antagonists of use in the present invention include acid addition salts which may, for example, be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid or phosphoric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also contemplates salts thereof, preferably non-toxic pharmaceutically acceptable salts thereof, such as the sodium, potassium and calcium salts thereof.

Suitable opioid analgesics of use in the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof.

A particularly preferred opioid analgesic of use in the present invention is morphine; or a pharmaceutically acceptable salt thereof.

Suitable pharmaceutically acceptable salts of the opioid analgesics of use in the present invention include those salts described above in relation to the salts of selective NMDA NR2B antagonists.

Preferred salts of opioid analgesics of use in the present invention include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

A particularly preferred opioid analgesic of use in the present invention is morphine hydrochloride.

As stated above, the selective NMDA NR2B antagonist and opioid analgesic may be formulated in a single pharmaceutical composition or alternatively in individual pharmaceutical compositions for simultaneous. separate or sequential use in accordance with the present invention.

Preferably the compositions according to the present invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water. to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings. such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil. is well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a selective NMDA NR2B antagonist, as the active ingredient. in association with a surface-active agent (or wetting agent or surfactant) or in the form of an emulsion (as a water-in-oil or oil-in-water, emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil. corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m, and have a pH in the range of 5.5 to 8.0.

Particularly preferred emulsion compositions are those prepared be mixing a selective NMDA NR2B antagonist with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a selective NMDA NR2B antagonist and an opioid analgesic, which process comprises bringing a selective NMDA NR2B antagonist and an opioid analgesic into association with a pharmaceutically acceptable carrier or excipient.

When administered in combination, either as a single or as separate pharmaceutical composition(s), the selective NMDA NR2B antagonist and the opioid analgesic are presented in a ratio which is consistent with the manifestation of the desired effect. In particular, the ratio by weight of the selective NMDA NR2B antagonist to the opioid analgesic will suitably be approximately 1 to 1. Preferably this ratio will be between 0.001 to 1 and 1000 to 1, and especially between 0.01 to 1 and 100 to 1.

A suitable dosage level for the selective NMDA NR2B antagonist is about 0.001 to 25 mg/kg per day, preferably about 0.005 to 10 mg/kg per day, and especially about 0.005 to 5 mg/kg per day. The compounds may be administered on a regimen of up to 6 times per day, preferably 1 to 4 times per day.

The opioid analgesic may be administered at a dosage level up to conventional dosage levels for such analgesics, but preferably at a reduced level in accordance with the present invention. Suitable dosage levels will depend upon the analgesic effect of the chosen opioid analgesic, but typically suitable levels will be about 0.001 to 25 mg/kg per day, preferably 0.005 to 10 mg/kg per day, and especially 0.005 to 5 mg/kg per day. The compound may be administered on a regimen of up to 6 times per day, preferably 1 to 4 times per day.

It will be appreciated that the amount of a selective NMDA NR2B antagonist and opioid analgesic required for use in the treatment or prevention of pain or nociception will vary not only with the particular compounds or compositions selected but also with the route of administration. the nature of the condition being treated, and the age and condition of the patient, and will ultimately be at the discretion of the attendant physician.

The following examples illustrate pharmaceutical compositions according to the invention.

These formulations may be prepared with separate active ingredients or with with a combination of active ingredients in one composition. In such combined preparations, the ratio of selective NMDA NR2B antagonist to opioid analgesic will depend upon the choice of active ingredients.

EXAMPLE 1A

Tablets Containing 1–25 mg of Compound

|  | Amount mg | | |
| --- | --- | --- | --- |
| Active Ingredients(s) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 1B

Tablets Containing, 26–100 mg of Compound

|  | Amount mg | | |
| --- | --- | --- | --- |
| Active Ingredients(s) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The active ingredient(s) cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 2

Parenteral Injection

|  | Amount |
| --- | --- |
| Active Ingredient(s) | 1 to 100 mg |
| Citric Acid Monohydrate | 0.75 mg |
| Sodium Phosphate | 4.5 mg |
| Sodium Chloride | 9 mg |
| Water for injection | to 10 ml |

The sodium phosphate, citric acid monohydrate and sodium chloride are dissolved in a portion of the water. The active ingredient(s) is (are) dissolved or suspended in the solution and made up to volume.

EXAMPLE 3

Topical Formulation

|  | Amount |
| --- | --- |
| Active Ingredient(s) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The active ingredient(s) is (are) is added and stirring continued until dispersed. The mixture is then cooled until solid.

EXAMPLE 4A (Surface-Active Agent) Injection Formulation

| Active Ingredient(s) | up to 10 mg/kg |
| --- | --- |
| Tween 80 ™ | up to 2.5% |

[in 5% aqueous mannitol (isotonic)]

The active ingredient(s) is (are) dissolved directly in a solution of the commercially available Tween 80™ (polyoxyethylenesorbitan monooleate) and 5% aqueous mannitol (isotonic).

EXAMPLE 4B (Emulsion) Injection Formulation

| Active Ingredient(s) | up to 30 mg/ml |
| --- | --- |
| Intralipid ™ (10–20%) |  |

The active ingredient(s) is (are) dissolved directly in the commercially available Intralipid™ (10 or 20%) to form an emulsion.

EXAMPLE 4C

Alternative (Emulsion) Injectable Formulation

|  | Amount |
| --- | --- |
| Active Ingredient(s) | 0.1–10 mg |
| Soybean oil | 100 mg |
| Egg Phospholipid | 6 mg |
| Glycerol | 22 mg |
| Water for injection | to 1 ml |

All materials are sterilized and pyrogen free. The active ingredient(s) is (are) dissolved in soybean oil. An emulsion is then formed by mixing this solution with the egg phospholipid, glycerol and water. The emulsion is then sealed in sterile vials.

The following Example illustrates that selective NMDA NR2B receptor antagonists have a reduced motor side-effect profile when compared with NMDA/glycine antagonists.

EXAMPLE 5

The present Example examined whether NMDA NR2B receptor antagonists have an improved therapeutic window over unselective NMDA/glycine antagonists and other ion channel blockers including lamotrigine and gabapentin, by comparing their anti-algesic effects with their liability to induce motor impairment in rats. Anti-algesic activity was assessed using an assay of neuropathic pain in rats (sciatic nerve ligation) and in a carrageenan-induced hyperalgesia assay. Motor impairment was measured using an accelerating rotarod.

Methods

For sciatic nerve ligation, male Sprague Dawley rats (180–220 g) were anaesthetised with isofluorane, the left sciatic nerve exposed and 4 chromic catgut (4.0) ligatures were tied loosely around the nerve (spaced 1–2 mm apart) immediately proximal to the point of trifurcation. In sham-operated animals, the same dissection was performed but without ligation. Responses to mechanical pressure were assessed 7 days after ligation using a modified Randall-Selitto algesiometer in which constant force of 40 mmHg was applied to the hind paw and the latency to struggle was recorded as the reaction time. Mechanical allodynia was defined as the difference in reaction time for sham and ligature rats. Reaction times for drug treated rats were expressed as a percentage of this response. Compounds were administered 1 h before the test. In the carrageenan-induced hyperalgesia assay, male Sprague Dawley rats (100–120 g) received an intraplantar injection of carrageenan (4.5 mg) and mechanical thresholds were determined 3 h later using a modified Ugo Basile Algesiometer. Control rats received saline (0.15 ml i.pl.). Hyperalgesia was defined as the difference in vocalisation threshold for saline- and carrageenan-injected rats. Paw pressure scores for drug-treated rats were expressed as a percentage of this response. Compounds were administered 2 h after carrageenan. To determine the effects of the compounds on motor co-ordination, male Sprague Dawley rats (160–180 g) were first trained to remain for 120 s on the rotarod apparatus revolving at 12 r.p.m. on the morning before the test. Animals then received drug treatments and 1 h later were placed on an accelerating rotarod (increasing from 4–40 r.p.m. during a 5 min period) and the time the rats were able to remain on the rotarod recorded. Lamotrigine, gabapentin and (±)-CP-101,606 were suspended in 0.5% methocel and administered orally (1 ml/kg). Ifenprodil, L-701.324, L-687, 414 and (±)-Ro25-6981 were dissolved or suspended in in 0.5% methocel and administered intraperitoneally (1 ml/kg). MK-801 was dissolved in distilled water and given i.p. (1 ml/kg). Doses of compounds refer to the free base.

Results

Anti-algesia Studies

Animals with sciatic nerve ligation exhibited mechanical allodynia as measured by the reduction in the reaction time to withdraw the injured limb from the paw pressure apparatus Reaction times for sham and ligature rats were typically 22±1s and 8±1s. respectively. The NMDA NR2B antagonists, (±)-CP-101,606 and (±)-Ro25-6981, the NMDA/glycinie receptor antagonist L-701,324 and partial agonist L-687,414 and the non-competitive NMDA antagonist MK-801 dose-dependently reversed mechanical allodynia induced by sciatic nerve ligation (Table 1). Similarly, the novel anti-convulsant drugs, lamotrigine and gabapentin, and the vasodilator ifenprodil, which has affinity for the NMDA NR2B receptor, reversed mechanical allodynia. The order of potency was: MK-801>L-701,324>(±)-Ro25-6981>(±)-CP-101,606>ifenprodil>L-687,414>lamotrigine>gabapentin.

Intraplantar injection of carrageenan (4.5 mg) induced marked paw oedema and hyperalgesia to mechanical compression of the inflamed hind paw. All the compounds caused a dose-dependent inhibition of mechnical hyperalgesia induced by carrageenan (Table 1). The order of potency was: MK-801>L-701,324>(±)-Ro25-6981>ifenprodil>(±)-CP-101,606>L-687,414=gabapentin>lamotrigine.

Effects on Behaviour and Motor Co-ordination

Vehicle-treated rats were able to remain on the accelerating rotarod for approximately 140 s. MK-801 dose-dependently induced impairments in rotarod performance with an $ID_{50}$ of 0.22 mg/kg i.p. Body rolling. and head weaving were also observed following 0.3 and 1 mg/kg doses of MK-801. The NMDA/glycine receptor antagonist L-701,324 and partial agonist L-687,414 also induced rotarod deficits ($ID_{50}$ of 1.9 mg/kg i.p. and 53.3 mg/kg i.p.); ataxia was evident at 10 and 30 mg/kg i.p. of L-701,324 and L-687,414 induced body rolling and ataxia at 100 and 300 mg/kg i.p. Ifenprodil caused approximately 50% impairment in rotarod performance at 50 mg/kg, however, severe adverse effects were also observed at this dose (ptosis, pilorecetion, hypoactivitly and hyperventilation). Gabapentin caused motor impairments (ataxia) at doses of 30–300 mg/kg ($ID_{50}$ for rotarod was 133 mg/kg i.p.). Administration of lamotrigine at 500 mg/kg p.o. caused a 40% inhibition in the time spent on the rotarod: no other effects were observed at this dose. Similarly, (±)-Ro25-6981 induced a 47% inhibition of rotarod performance at a (lose of 100 mg/kg i.p. (±)-CP-101,606 did not inhibit motor performance on the rotarod up to 300 mg/kg p.o.; in fact, there was a significant increase in latency following 300 mg/kg dose compared to vehicle-treated rats.

The ratios for the $ID_{50}$ inducing motor impairment and inhibition of allodynia in neuropathic rats were at least 4 fold greater for the NMDA NR2B receptor antagonists, (±)-CP-101,606 (ratio>49) and (±)-Ro25-6981 (ratio>26), than were found for MK-801 (ratio 1.1), the NMDA/glycine antagonists (ratio<6), gabapentin (ratio 1.5) and ifenprodil (ratio 5.3). Lamotrigine had a similar profile to that of the NMDA NR2B receptor antagonists (ratio>45).

Conclusions

These data suggest that NMDA NR2B antagonists may be useful for treating neuropathic pain in man with an improved therapeutic window over clinically used unselective ion channel blockers.

TABLE 1

Summary of the anti-algesic and ataxic properties of NMDA receptor antagonists and other ion channel blockers

| | $ID_{50}$ (mg/kg) | | | |
|---|---|---|---|---|
| | Antinociception | | Motor Impairment | Ratio |
| | Rat Ligation | Rat Carrageenan | Rat Rotarod | Rotarod/Rat Ligation |
| Lamotrigine (p.o.) | 11 | 207 | >500 | >45 |
| Gabapentin (p.o.) | 87 | 50 | 133 | 1.5 |
| Ifenprodil (i.p.) | 9.5 | 17 | ≧50 | 5.3 |
| MK-801 (i.p.) | 0.19 | 0.21 | 0.22 | 1.1 |
| L-701,324 (i.p.) | 2.6 | 2.5 | 1.9 | 0.7 |
| L-687,414 (i.p.) | 9.8 | 50 | 53 | 5.4 |
| (±)-CP-101,606 (p.o.) | 6.1 | 37 | >300 | >49 |
| (±)-Ro25-6981 (i.p.) | 3.8 | 5.7 | ≧100 | ≧26 |

The following Example demonstrates the synergistic antinociceptive effects of a combined treatment of the selective NMDA NR2B antagonist (±)-Ro25-6981 with morphine.

EXAMPLE 6

The present Example examined whether the NMDA NR2B antagonist (±)-Ro25-6981 could potentiate the antinociceptive effects of morphine in an assay of inflammatory hyperalgesia in rats to determine whether such combination therapies may provide improved analgesic efficacy with reduced side-effects in man.

Methods

Male Sprague Dawley rats (100–120 g) received an intraplantar injection of carrageenan (4.5 mg) and mechanical thresholds were determined 3 h later using a modified Ugo Basile Algesiometer. Control rats received saline (0.15 ml i.pl.). Hyperalgesia was defined as the difference in vocalisation threshold for saline- and carrageenan-injected rats. Paw pressure scores for drug-treated rats were expressed as a percentage of this response. Compounds were administered 2 h after carrageenan. To determine the effects of morphine and (±)-Ro25-6981 on motor co-ordination, male Sprague Dawley rats (160–180 g) were first trained to remain for 120 s on the rotarod apparatus revolving at 12 r.p.m. on the morning before the test. Animals then received drug treatments and 1 h later were placed on an accelerating rotarod (increasing from 4–40 r.p.m. during a 5 min period) and the time the rats were able to remain on the rotarod recorded.

(±)-Ro25-6981 was suspended in 0.5% methocel and administered intraperitoneally (1 ml/kg). Morphine HCl was dissolved in saline and given subcutaneously (1 ml/kg). Doses of compounds refer to the free base.

Results

Effect of Ro25-6981 on Carrageenan-Induced Hyperalgesia

Figure 1:
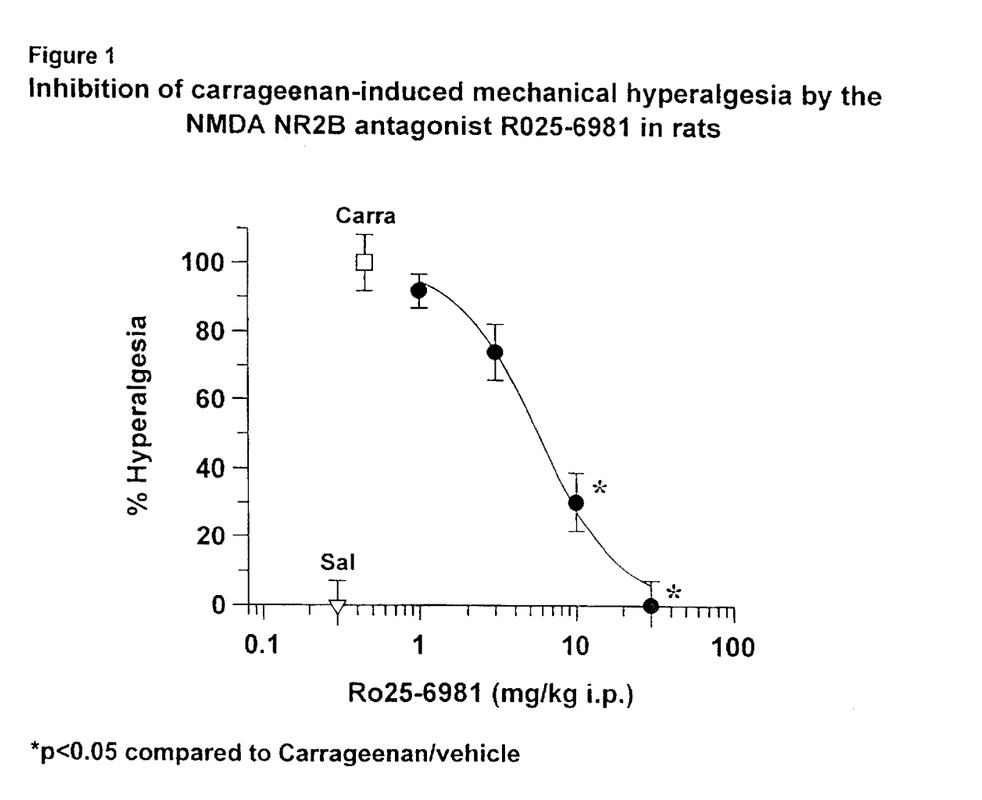
FIG. 1 is a graph of the carrageenan-induced mechanical hyperalgesia (plotted as a percent) as a function of NMDA NR2B antagonist dose (mg/kg i.p.).

Intraplantar injection of carrageenan (4.5 mg) induced marked paw oedema and hyperalgesia to mechanical compression of the inflamed hind paw. Intraperitoneal (i.p.) administration (±)-Ro25-6981 caused a dose-dependent reversal of mechanical hyperalgesia induced by carrageenan at doses of 10 and 30 mg/kg (FIG. 1). A dose of 1 mg/kg was chosen for combination experiments as this did not cause significant antinociception.

Combination of Ro25-6981 and Morphine oil Carrageenan-Induced Hyperalgesia

Figure 2:
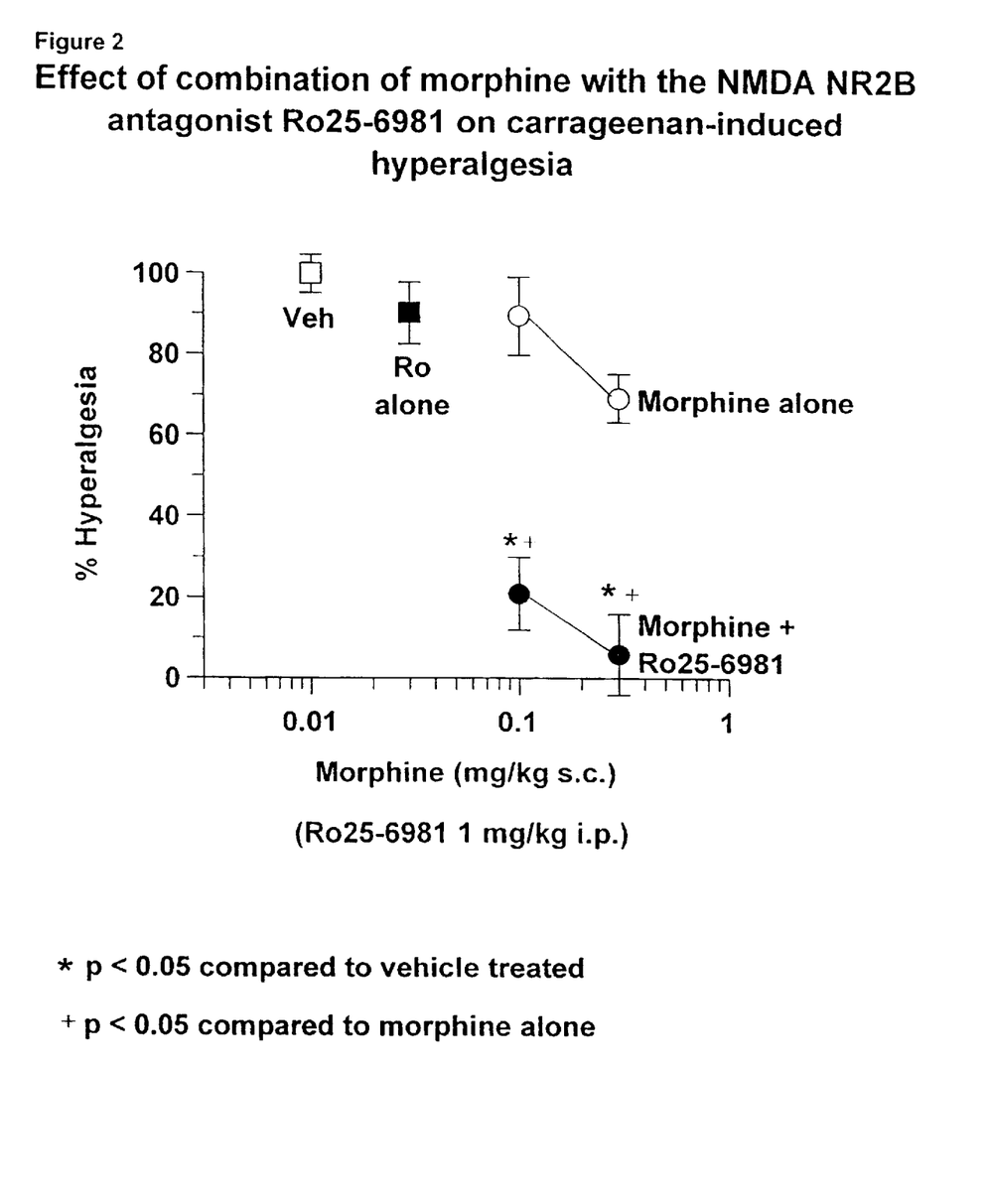
FIG. 2 is a graph of the percent hyperalgesia as a function of a NOVA NR2B antagonist alone, morphine alone, and the combination of morphine with an NMDA NR2B antagonist.

Subcutaneous (s.c.) administration of morphine alone at 1 mg/kg completely reversed mechanical hyperalgesia induced by carrageenan whereas lower doses of 0.1 and 0.3 mg/kg were without effect (FIG. 2). Combined-administration of a subthreshold dose of (±)-Ro2,5-6981 (1 mg/kg, i.p.) with a subthreshold doses of morphine (0.1 and 0.3 mg/kg) resulted in a significantly greater inhibition of hyperalgesia (FIG. 2). The percent inhibition following a dose of 0.1 mg/kg of morphine was increased from 11% to 80% and following a dose of 0.3 mg/kg from 31% to 94%.

Combination of Ro25-6981 with Morphine on Rotarod Performance

Figure 3:
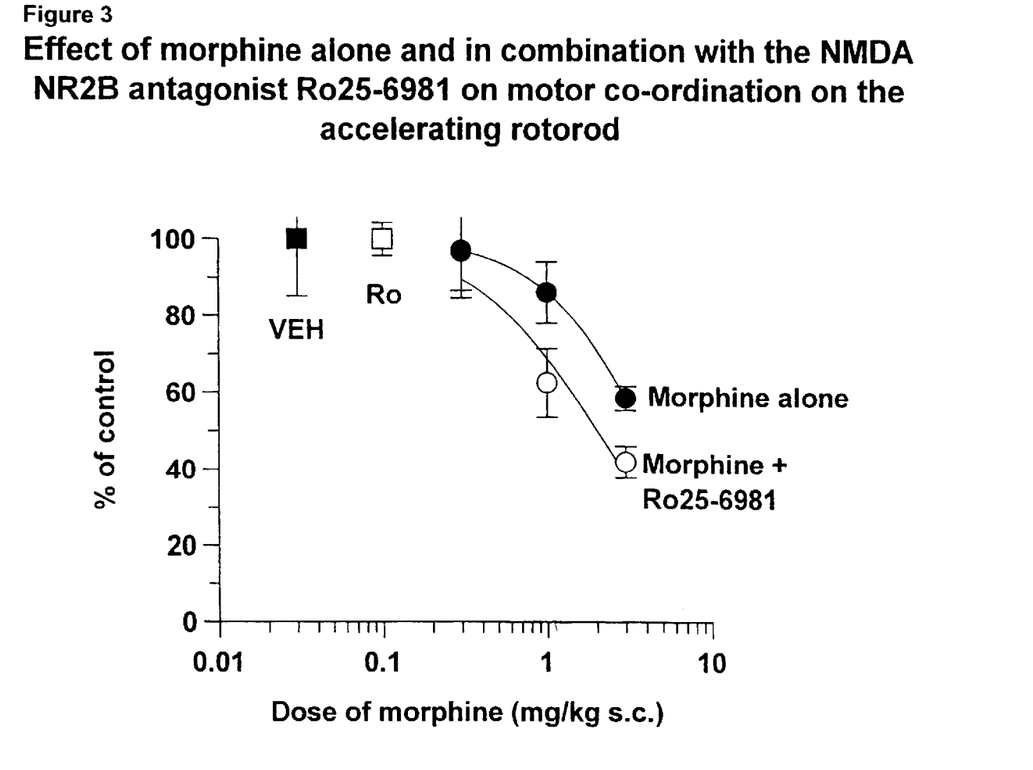
FIG. 3 is a graph of motor control as a function of a NMDA NR2B antagonist alone, morphine alone, and the combination of morphine with an NMDA NR2B antagonist.

Treatment with (±)-Ro25-6981, (1 mg/kg i.p.) alone had no effect on rotarod performance (FIG. 3). Treatment with morphine alone at 3 mg/kg s.c. induced a significant impairment in rotarod performance whereas lower doses of 0.3 and 1 mg/kg had no effect (FIG. 3). Similarly, when combined with (±)-Ro25-6981 (1 mg/kg i.p.), the minimum effective dose of morphine causing rotarod disruption was 3 mg,/kg (FIG. 3).

Conclusions

These data demonstrate that administration of (±)-Ro25-6981, at a dose that is ineffective by itself, can markedly potentiate the antinociceptive effects of morphine. In contrast, there was no significant interaction between (i)-Ro25-6981 (1 mg/kg) and morphine (0.3–3 mg/kg) on the rotarod indicating that motor impairment induced by morphine is not potentiated by (±)-Ro25-6981.

What is claimed is:

1. A synergistic product consisting essentially of a synergistic amount of a selective NMDA (N-methyl-D-aspartate) NR2B subtype antagonist and an opioid analgesic as a combined preparation for simultaneous, separate or sequential use in the treatment of pain or nociception, wherein said selective NMDA NR2B subtype antagonist is eliprodil.

2. The synergistic, product according to claim 1 wherein the opioid analgesic is morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof.

3. The synergistic product according to claim 2 wherein the opioid analgesic is morphine or a pharmaceutically acceptable salt thereof.

4. A synergistic pharmaceutical composition consisting essentially of a synergistic amount of a selective NMDA (N-methyl-D-aspartate) NR2B subtype antagonist and an opioid analgesic together with at least one pharmaceutically acceptable carrier or excipient, wherein said NMDA NR2B subtype antagonist is eliprodil.

5. A method for the treatment or prevention of pain or nociception, which method comprises administering a synergistic pharmaceutical composition of claim 4 a synergistic to a patient in need of such treatment of amount of a selective NMDA (N-methyl-D-aspartate) NR2B subtype antagonist and an opioid analgesic such that together they give effective pain relief, wherein said selective NMDA NR2B subtype antagonist is eliprodil.

6. A process for the preparation of a synergistic pharmaceutical composition consisting essentially of a synergistic amount of a selective NMDA (N-methyl-D-aspartate) NR2B subtype antagonist and an opioid analgesic, which process comprises bringing a selective NMDA NR2B antagonist and an opioid analgesic into association with a pharmaceutically acceptable carrier or excipient, wherein said selective NMDA NR2B subtype antagonist is eliprodil.

* * * * *